United States Patent [19]

Artmeier

[11] Patent Number: 5,199,420

[45] Date of Patent: Apr. 6, 1993

[54] LITHOTRITOR ARRANGEMENT

[75] Inventor: Theo Artmeier, Gröbenzell, Fed. Rep. of Germany

[73] Assignee: Dornier Medizintechnik GmbH, Fed. Rep. of Germany

[21] Appl. No.: 729,604

[22] Filed: Jul. 15, 1991

[30] Foreign Application Priority Data

Jul. 14, 1990 [DE] Fed. Rep. of Germany ....... 4022496

[51] Int. Cl.$^5$ ............................................. A61B 17/22
[52] U.S. Cl. ............................................. 128/24 EL
[58] Field of Search ............... 128/24 EL, 660.03; 74/431, 444, 457

[56] References Cited

U.S. PATENT DOCUMENTS

| | | | |
|---|---|---|---|
| 4,796,613 | 1/1989 | Heumann et al. | 128/24 EL |
| 4,877,017 | 10/1989 | Hahn et al. | 128/24 EL |
| 5,036,836 | 8/1991 | Terai et al. | 128/24 EL |
| 5,044,354 | 9/1991 | Goldhorn et al. | 128/24 EL |
| 5,072,721 | 12/1991 | Weiler et al. | 128/24 EL |
| 5,078,124 | 1/1992 | Viebach et al. | 128/24 EL |

FOREIGN PATENT DOCUMENTS

| | | |
|---|---|---|
| 551149 | 12/1959 | Belgium. |
| 0006193 | 1/1980 | European Pat. Off.. |
| 0286170 | 10/1988 | Fed. Rep. of Germany ... 128/24 EL |
| 3737858 | 5/1989 | Fed. Rep. of Germany ... 128/24 EL |

Primary Examiner—Lee S. Cohen
Assistant Examiner—K. M. Pfaffle
Attorney, Agent, or Firm—Evenson, McKeown, Edwards & Lenahan

[57] ABSTRACT

An arrangement for treating patients by means of focussed shock waves, particularly lithotritors, having a therapy head which is fastened to a housing by means of an arm and comprises devices for generating, focussing and introducing shock waves into the body of a patient, the therapy head being fastened to the arm by means of a gearing.

8 Claims, 4 Drawing Sheets

LITHOTRITOR ARRANGEMENT

BACKGROUND AND SUMMARY OF THE INVENTION

The invention relates to an arrangement for treating patients by means of focussed shock waves, particularly lithotritors, having a therapy head which is fastened by means of an arm to a housing and includes devices for generating, focussing and introducing shock waves into a patient's body, the axis of the therapy head being movable on a conical envelope, the tip of which is situated in the focal point of the therapy head (isocenter). An apparatus of this type is known from the European Patent Document EP 0 286 170.

It is an object of the invention to kinematically improve such an arrangement with respect to the locating, the positioning and the treatment of the patient.

According to the invention, this object is achieved by means of an arrangement wherein the axis of the therapy head is movable on the enclosure of a cone, the tip of which is in the focal point isocenter of the therapy head, and wherein the therapy head is fastened to the arm by means of a gearing mechanism.

The therapy head is arranged in such a manner that it is movable on the envelope of a cone, the tip of the conical envelope coinciding with the focal point of the therapy head (isocentric movement). The envelope of the cone, according to the invention, is situated such that one of its generatrices extends perpendicularly, that is, that the therapy head can also be brought into a position in which its longitudinal axis extends perpendicularly so that the treatment of gallstones also becomes possible.

A gearing swivels the therapy head on the conical envelope in such a manner that it does not carry out any rotation about its longitudinal axis with respect to the overall apparatus. Thus unintentional shifts are avoided when taking up the locating.

In an embodiment of the invention, an ultrasonic locating device is fastened to the therapy head in such a manner that its center axis constantly aims at the focal point of the therapy head. This has the advantage that, in the ultrasonic image, the focal point is always in the center line whereby the locating is significantly simplified. The physician is relatively free to search for windows for the ultrasonic image on the patient's body and in this case does not lose the focus from the center of the image.

Other objects, advantages and novel features of the present invention will become apparent from the following detailed description of the invention when considered in conjunction with the accompanying drawings.

DETAILED DESCRIPTION OF THE DRAWINGS

Figure 1:
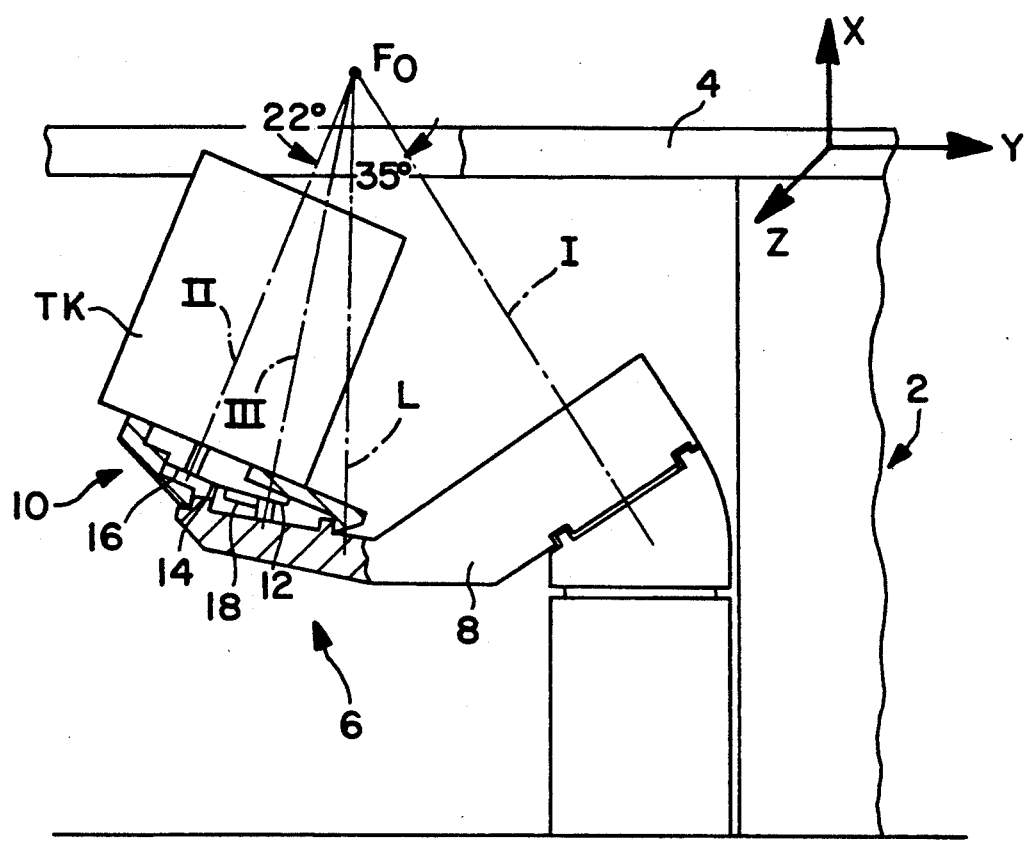
FIG. 1 is a basic schematic diagram of an arrangement according to the invention with a sectional representation of a gearing.

The apparatus :or the treatment of concrements illustrated in FIG. 1 comprises a housing 2; a reclining device 4 for the patient which is provided with recesses and by means of a motor or by hand can be shifted in the x-, y-, z-direction; as well as of treating apparatus 6 which will be described in detail in the following.

An arm 8 is rotatably fastened to the housing of the treatment apparatus. The axis of rotation I extends at an angle of 35° with respect to the vertical line (L). The arm 8 is bent and, at its other end, carries a therapy head TK, a differential gearing 10 being disposed between the arm 8 and the therapy head TK. The differential gearing comprises three gearwheels 12, 14, 16, gearwheel 12 being rigidly fastened to the arm 8; and gearwheel 16 being rigidly connected with the therapy head TK. The differential gearwheel 14 is held on the arm 8 by means of a crank 18.

Figure 2:
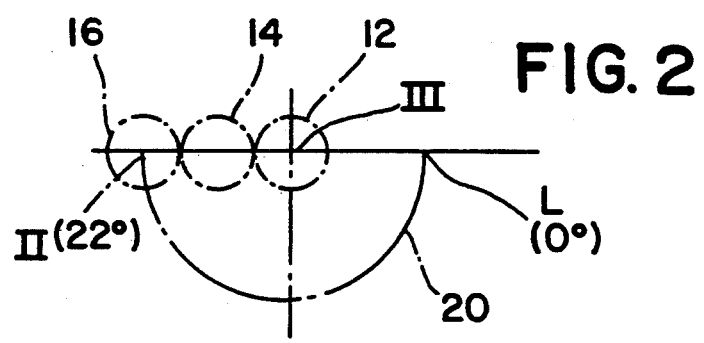
FIG. 2 is schematic top view of the gearing of FIG. 1.

FIG. 2 illustrates a part of the path 20 on which the therapy head TK moves when it is swivelled. During the movement on the path 20, the gearing 10 has the effect that the therapy head TK carries out no rotation about its axis II when the gearwheels 12, 14, 16, with respect to the number of their teeth and their reference diameter are equal to one another. The gearing therefore has the result that a fan-shaped ultrasonic locating device (not shown) which is integrated into the therapy head, continuously extends through the focal point Fo (isocenter) without changing the direction. The gearing 10 prevents a rotation of the therapy head TK about its axis II.

Figure 5:
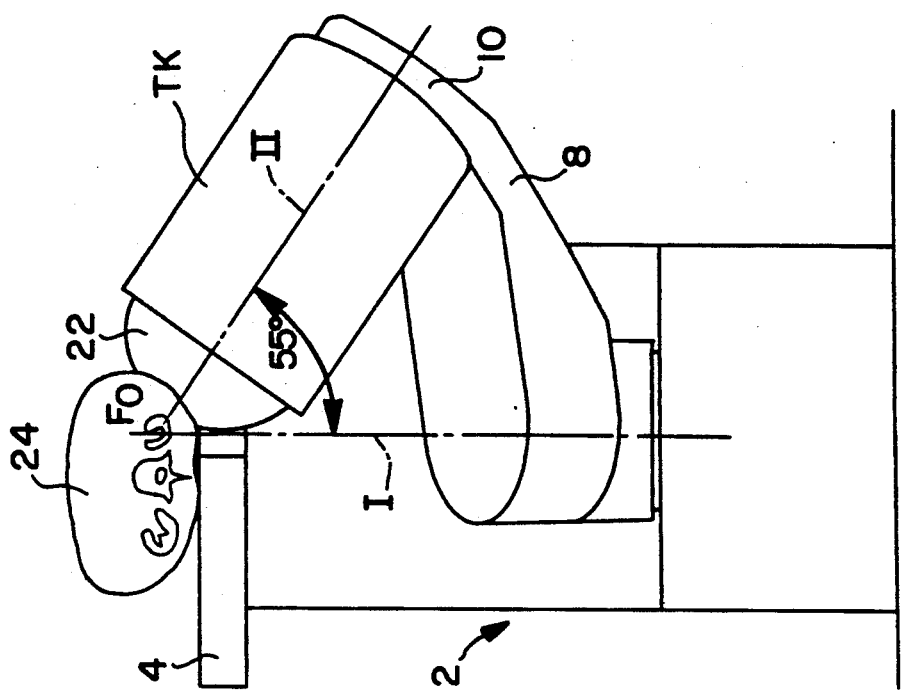
FIGS. 5 and 6 are respective views of the treatment position of the therapy head for treatment of a concrement in left kidney.
Figure 3:
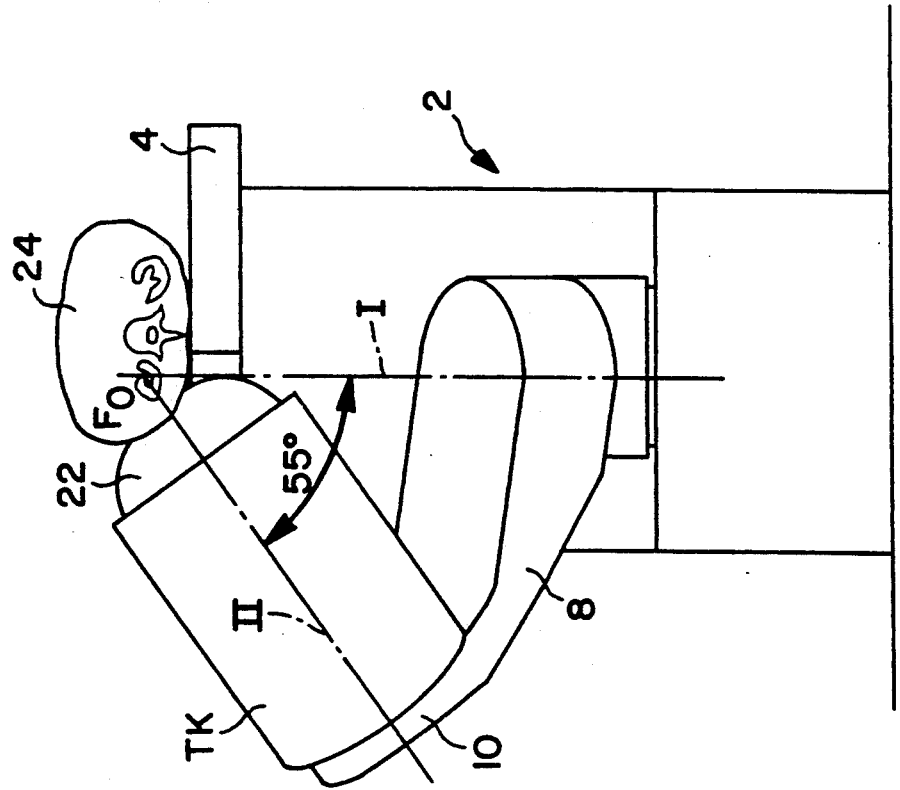
FIGS. 3 and 4 are respective views of the treatment position of the therapy head, shown for treatment of a concrement in right kidney.
Figure 7:
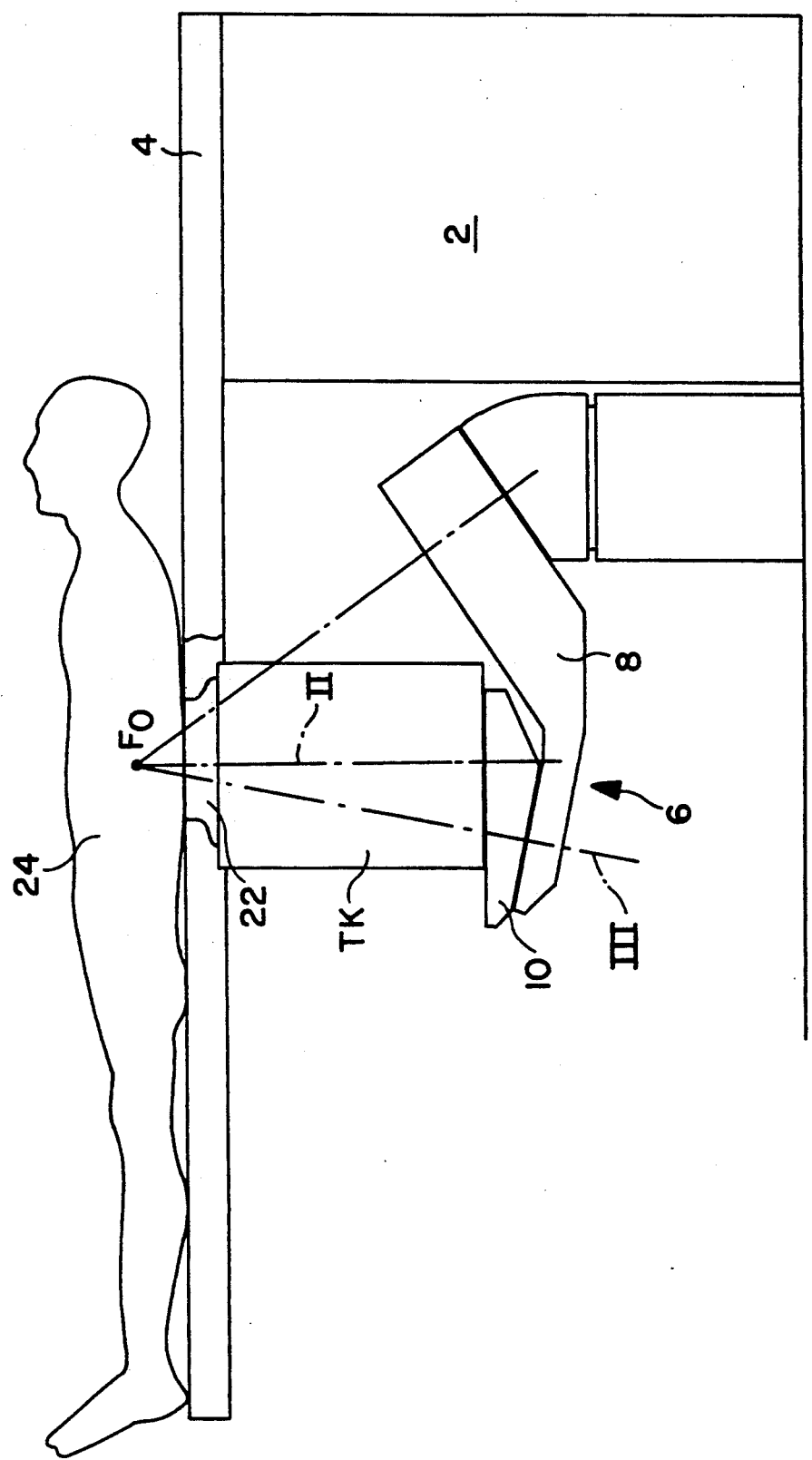
FIG. 7 is a view of the treatment position of the therapy head for treatment of a concrement in gall bladder.

When the therapy head TK moves about the axis III, the therapy head can be brought into a position perpendicular under a patient, as shown in FIG. 7. As illustrated in FIG. 1, the conical envelope of the axis of rotation II is 22°. In the case of this angle, together with the angle of 35° with respect to the vertical line (L), almost rectangular couplings are permitted to the right and the left kidney, as shown in FIGS. 3 and 5.

Figure 4:
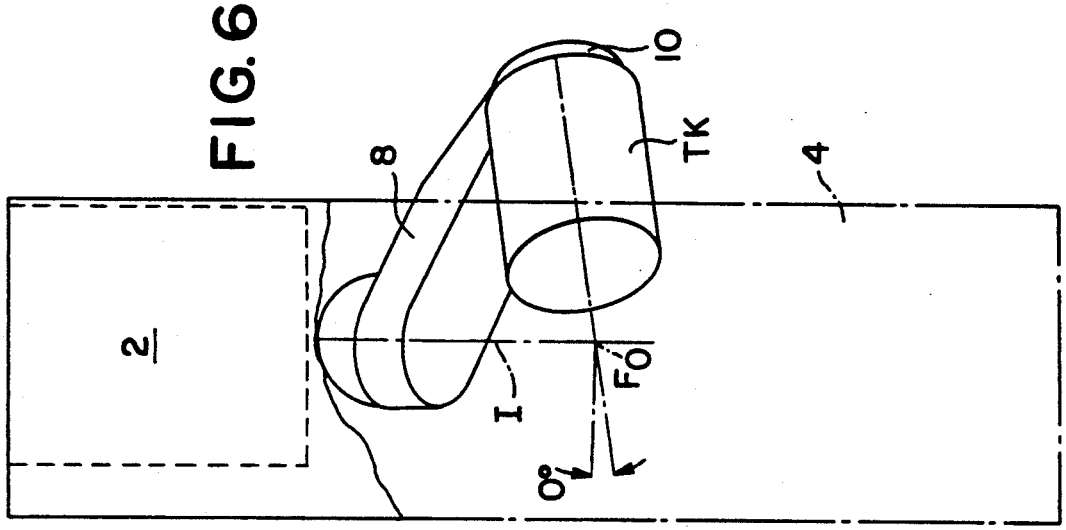
Figure 6:
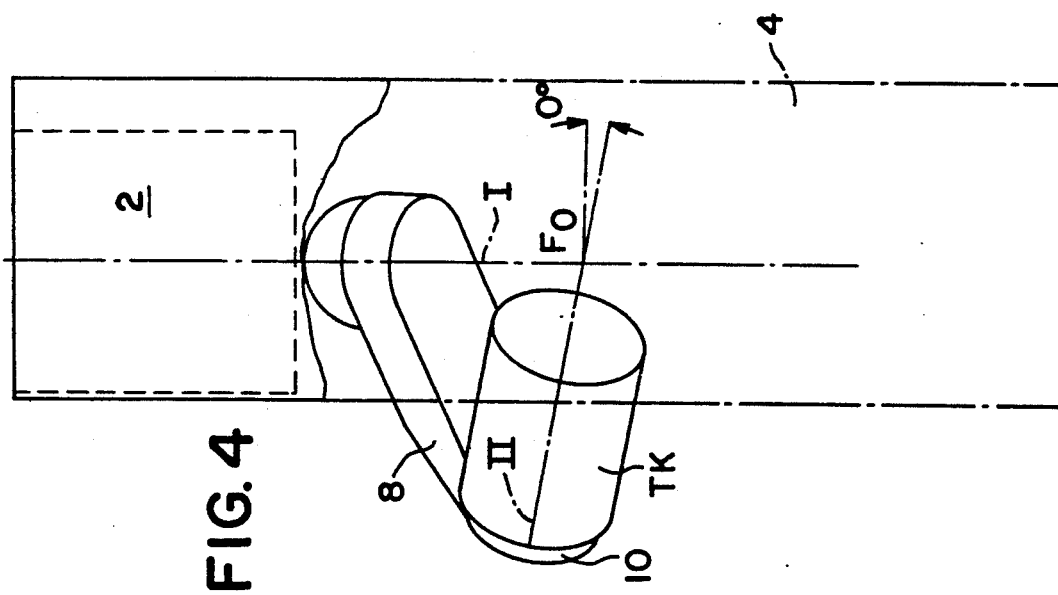

The angle of 55° shown there is obtained as the sum of the two above-mentioned angles. For the coupling-on, bellows 22 are also shown in FIGS. 3 and 5 which are elastically moved against the patient's body. The therapy position of FIGS. 3 and 5 is also shown in FIGS. 4 and 6 as a top view.

By means of the gearing 10, the therapy head TK may also be brought into a position perpendicularly under a patient, as shown in FIG. 7.

Although the invention has been described and illustrated in detail, it is to be clearly understood that the same is by way of illustration and example, and is not to be taken by way of limitation. The spirit and scope of the present invention are to be limited only by the terms of the appended claims.

I claim:

1. An arrangement for treating a patient with focussed shock waves, comprising:
   a housing;
   a therapy head that includes means for generating, focussing and introducing shock waves into the body of a patient, the therapy head having a focal point isocenter and an axis of rotation that is movable on an enclosure of a cone, the cone having a tip which is in the focal point of the isocenter;

an arm rotatably mounted on the housing and having an axis of rotation; and a gearing mechanism coupled between the arm and the therapy head to fasten the therapy head to the arm, wherein the gearing mechanism includes a toothed gearing which comprises a gearwheel fixedly connected with the arm, a rotatable differential gearwheel, a crank which fastens the rotatable differential gearwheel to the arm, and a gearwheel fastened to the therapy head.

2. An arrangement according to claim 1, wherein a number of teeth and a reference diameter of each of said gearwheels of the gearing mechanism are equal to one another.

3. An arrangement according to claim 2, wherein the gearing mechanism includes a gearing housing and bearings, the gearing housing being disposed via said bearings on the arm and on the therapy head.

4. An arrangement according to claim 1, wherein an axis of rotation of the therapy head and the axis of the gearwheel fixedly connected with the arm form an angle of approximately 11 degrees with one another, and the axis of rotation of the arm on the housing has an angle or 35 degrees with respect to a line that is normal to a longitudinal axis of the patient.

5. An arrangement according to claim 2, wherein the axis of rotation of the therapy head and an axis of the gearwheel fixedly connected with the arm form an angle of approximately 11 degrees with one another, and the axis of rotation of the arm on the housing has an angle or 35 degrees with respect to a line that is normal to a longitudinal axis of the patient.

6. An arrangement for treating a patient with focussed shock waves, comprising:

a housing;

a therapy head that includes means for generating, focussing and introducing shock waves into the body of a patient, the therapy head having a focal point isocenter and an axis that is movable on an enclosure of a cone, the cone having a tip which is in the focal point of the isocenter;

an arm rotatably mounted on the housing and having an axis of rotation, the axis of rotation of the arm extending through the isocenter; and a gearing mechanism coupled between the arm and the therapy head to fasten the therapy head to the arm, wherein the gearing mechanism includes a toothed gearing which comprises a gearwheel fixedly connected with the arm, a rotatable differential gearwheel, a crank which fastens the rotatable differential gearwheel to the arm, and a gearwheel fastened to the therapy head.

7. An arrangement according to claim 6, wherein a number of teeth and a reference diameter of each of said gearwheels of the gearing mechanism are equal to one another.

8. An arrangement according to claim 7, wherein the gearing mechanism includes a gearing housing and bearings, the gearing housing being disposed via said bearings on the arm and on the therapy head.

* * * * *